US00PP18350P2

(12) United States Plant Patent
Baan

(10) Patent No.: US PP18,350 P2
(45) Date of Patent: Dec. 25, 2007

(54) ***HELICONIA* PLANT NAMED 'LARS'**

(50) Latin Name: *Heliconia psittacorum*
Varietal Denomination: Lars

(75) Inventor: Robert Jacob Pieter Baan, Enkhuizen (NL)

(73) Assignee: Plant Planet BV, Warmenhuizen (NL)

( * ) Notice: Subject to any disclaimer, the term of this patent is extended or adjusted under 35 U.S.C. 154(b) by 10 days.

(21) Appl. No.: 11/366,071

(22) Filed: Mar. 2, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

UPOV–ROM GTITM, Plant Variety Database, 2006/04, GTI Jouve Retrieval Software, Citation for *Heliconia* 'Lars' one page.*

Plant Planet, retrieved from the Internet on Mar. 15, 2007 <http://www.plantplanet.nl/Engeland/index_en.htm> 2 pages.*

* cited by examiner

*Primary Examiner*—Kent Bell
*Assistant Examiner*—June Hwu

(57) ABSTRACT

A new cultivar of *Heliconia* plant named 'Lars' that is characterized by a compact habit and small orange flowers that bloom throughout the entire year.

1 Drawing Sheet

Botanical classification: *Heliconia psittacorum.*
Variety denomination: 'Lars'.

BACKGROUND OF THE INVENTION

The present invention relates to a new and distinct cultivar of *Heliconia* plant botanically known as *Heliconia psittacorum* and hereinafter referred to by the cultivar name 'Lars'.

The new cultivar was discovered as a naturally occurring whole plant mutation in a cultivated area of Enkhuizen, The Netherlands. The exact parent plant is unknown. The cultivar 'Lars' was discovered by the inventor in 1999 as a single plant.

Asexual reproduction first occurred when rhizomes of the new cultivar 'Lars' were propagated in 2000 in Enkhuizen, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Heliconia* cultivar 'Lars'. These traits in combination distinguish 'Lars' as a new and distinct cultivar apart from other existing known varieties of *Heliconia.*

1. *Heliconia* 'Lars' exhibits compact growth.
2. *Heliconia* 'Lars' exhibits orange flowers.
3. *Heliconia* 'Lars' exhibits small flowers.
4. *Heliconia* 'Lars' exhibits flowers that bloom throughout the entire year.

The closest comparison cultivar is the *Heliconia* species, *Heliconia psittacorum* sp. The new cultivar 'Lars' is distinguishable from *Heliconia psittacorum* sp. by the following characteristics:

1. *Heliconia* 'Lars' exhibits a more compact habit.
2. *Heliconia* 'Lars' exhibits smaller flowers.

3. *Heliconia* 'Lars' exhibits flowers that bloom throughout the entire year.

Plants of the species only bloom in summer.

BRIEF DESCRIPTION OF THE DRAWING

The accompanying photograph illustrates the distinguishing traits of *Heliconia* 'Lars'. The plant in the photograph shows an overall view of a 4 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Heliconia* cultivar named 'Lars'. Data was collected in Enkhuizen, The Netherlands from 4 month old glass greenhouse grown plants in 25 cm. diameter containers. The time of year was Fall and the temperature was kept at 22° Centigrade during the day and 20° Centigrade at night. The light level was natural outdoor light. The soil Ph was 5.8. Color determinations are in accordance with The Royal Horticultural Society Colour Chart 2001 edition, except where general color terms of ordinary dictionary significance are used. The growing requirements are similar to the species. 'Lars' has not been tested under all possible conditions and phenotypic differences may be observed with variations in environmental, climatic, and cultural conditions, however, without any variance in genotype.

Botanical classification: *Heliconia psittacorum* 'Lars'.
Use: Ornamental Perennial.
Parentage: The parent plant of 'Lars' is unknown.
Vigor: High.
Growth habit: Broad upright.

Plant shape: Narrow inverted triangle.
Suitable container size: 25 cm. diameter container.
Height: Average 87 cm. in height.
Width: Average 92 cm. in width.
Low temperature tolerance: USDA Zone 10.
High temperature tolerance: 40 degrees Centigrade.
Propagation: Rhizomes.
Time to initiate roots: 5 days during the summer and 10 days during the winter to initiate roots at 22 degrees Centigrade.
Time to produce a rooted cutting or liner: 42 days during the summer and 70 days during the winter at 22 degrees Centigrade.
Crop time: Approximately 4 months are required to produce a finished flowering plant.
Roots:
*Root color.*—199D.
*Root density.*—Not dense.
*Thick or fine.*—Thick.
*Root texture.*—Fleshy.
Stem:
*Branching habit.*—Freely branching with basal shoots.
*Average number of basal branches.*—17.
*Pinching.*—Not Required.
*Basal branch diameter.*—1.3 cm. in diameter.
*Basal branch length.*—50.2 cm. in length.
*Basal branch strength.*—Strong.
*Stem color.*—143A.
*Stem shape.*—Ovate.
*Pubescence.*—Absent.
*Internode length.*—11.8 cm. between nodes.
Foliage:
*Durability of foliage to stress.*—Moderate to high.
*Texture.*—Both sides glabrous and glossy.
*Leaf arrangement.*—Alternate.
*Compound or single.*—Single.
*Quantity of leaves per basal branch.*—6.
*Leaf shape.*—Lanceolate.
*Leaf apex.*—Apiculate.
*Leaf base.*—Unequal.
*Leaf length.*—Average 33.3 cm. in length.
*Leaf width.*—Average 8.7 cm. in width.
*Pubescence.*—Absent.
*Leaf margin.*—Entire.
*Young leaf color* (*lower surface*).—143A to 144A.
*Young leaf color* (*upper surface*).—143A to 144A.
*Mature leaf color* (*lower surface*).—137A to 139A.
*Mature leaf color* (*upper surface*).—139A.
*Vein color* (*lower surface*).—145A to 145B.
*Vein color* (*upper surface*).—137A.
*Venation pattern.*—Pinnate.
*Leaf attachment.*—Petiolate.
*Petiole dimensions.*—Average 12.2 mm. in length and 3.5 mm. in width.
*Petiole color upper side.*—137A.
*Petiole color lower side.*—137A.
*Petiole sheath length.*—20.8 cm. average.
*Petiole sheath width.*—9 mm. average.
*Petiole sheath color.*—143A, margins 177B to 177C.
Flower:
*Flower type.*—Single.
*Flower form.*—Cincinnus.
*Cincinnus height.*—8.6 cm.
*Cincinnus width.*—8.2 mm.
*Inflorescence arrangement.*—Terminal cincinnus, average of 3 per plant.
*Flowering habit.*—Continuous.
*Quantity of flowers per cincinnus.*—Average 16.
*Quantity of flower buds per cincinnus.*—Average 16.
*Quantity of flowers and buds per plant.*—Average 96.
*Time to flower.*—10 weeks.
*Fragrance.*—None.
*Flower bud length.*—3 cm. in length.
*Flower bud diameter.*—3.5 mm. in diameter.
*Flower bud shape.*—Oblong, narrow and triangular.
*Bud color.*—N25C, apex 147A.
*Rate of bud opening.*—50% for one week.
*Flower aspect.*—Upright to slightly outward.
*Flower shape.*—Tubular.
*Flower dimensions.*—7 mm. in diameter and 4 cm. in height.
*Flower longevity.*—Approximately 14 days.
*Petal appearance.*—Dull.
*Petal texture.*—Glabrous.
*Number of petals.*—3.
*Fused or unfused.*—Unfused.
*Petal arrangement.*—Rotate.
*Petal shape.*—Lanceolate.
*Petal margin.*—Entire.
*Petal apex.*—Acute.
*Petal dimensions.*—Average 4 mm. in length and 2 mm. in width.
*Petal color when opening* (*upper side*).—24C to 24D.
*Petal color when opening* (*under side*).—24C to 24D.
*Petal color fully opened* (*upper side*).—24C.
*Petal color fully opened* (*under side*).—24C.
*Petal color fading to.*—24D.
*Self-cleaning or persistent.*—Self-cleaning.
Sepals:
*Number of sepals.*—3.
*Sepal arrangement.*—Fused into a narrow, triangular tube.
*Sepal shape.*—Narrow lanceolate.
*Sepal margin.*—Entire.
*Sepal apex.*—Long acuminate.
*Sepal base.*—Cuneate.
*Sepal surface.*—Glabrous, shiny, and glossy.
*Sepal dimensions.*—Average 4 cm. in length and 5 mm. in width.
*Sepal color* (*young upper side*).—N25C, apex 147A.
*Sepal color* (*young under side*).—N25C, apex 147A.
*Sepal color* (*mature upper side*).—25A, apex 147A.
*Sepal color* (*mature under side*).—25A, apex 147A.
Calyx:
*Calyx shape.*—Tubular.
*Calyx dimensions.*—Average 4 cm. in length and 7 mm. in diameter.
Peduncle:
*Peduncle dimensions.*—Average 18.5 cm. in length and 2 mm. in diameter.
*Peduncle aspect.*—Rigid.
*Peduncle angle.*—0°.
*Peduncle shape.*—Straight upright.
*Peduncle texture.*—Smooth.
*Peduncle color.*—137A.
*Peduncle strength.*—Strong.
Pedicel:
*Pedicel length.*—1 cm.
*Pedicel diameter.*—1.5 mm.
*Pedicel angle.*—10°.
*Pedicel color.*—24A to 25B.
*Pedicel strength.*—Moderate.

Reproduction organs:

*Stamen number.*—Average 6.

*Anther shape.*—Linear.

*Anther dimensions.*—Average 6 mm. in length and 6 mm. in width.

*Anther color.*—23D, filament 24C.

*Amount of pollen.*—Low to moderate.

*Pollen color.*—23D.

*Pistil number.*—1.

*Pistil dimensions.*—Average 3.6 cm. in length.

*Stigma shape.*—Three-lobed.

*Stigma color.*—22A to 22B.

*Style length.*—3.5 mm.

*Style color.*—24C to 24D.

*Ovary color.*—24A to 25B with touches of 146B.

Disease and insect resistance: Disease and insect resistance have not been observed.

What is claimed is:

1. A new and distinct variety of *Heliconia* plant named 'Lars' as described and illustrated.

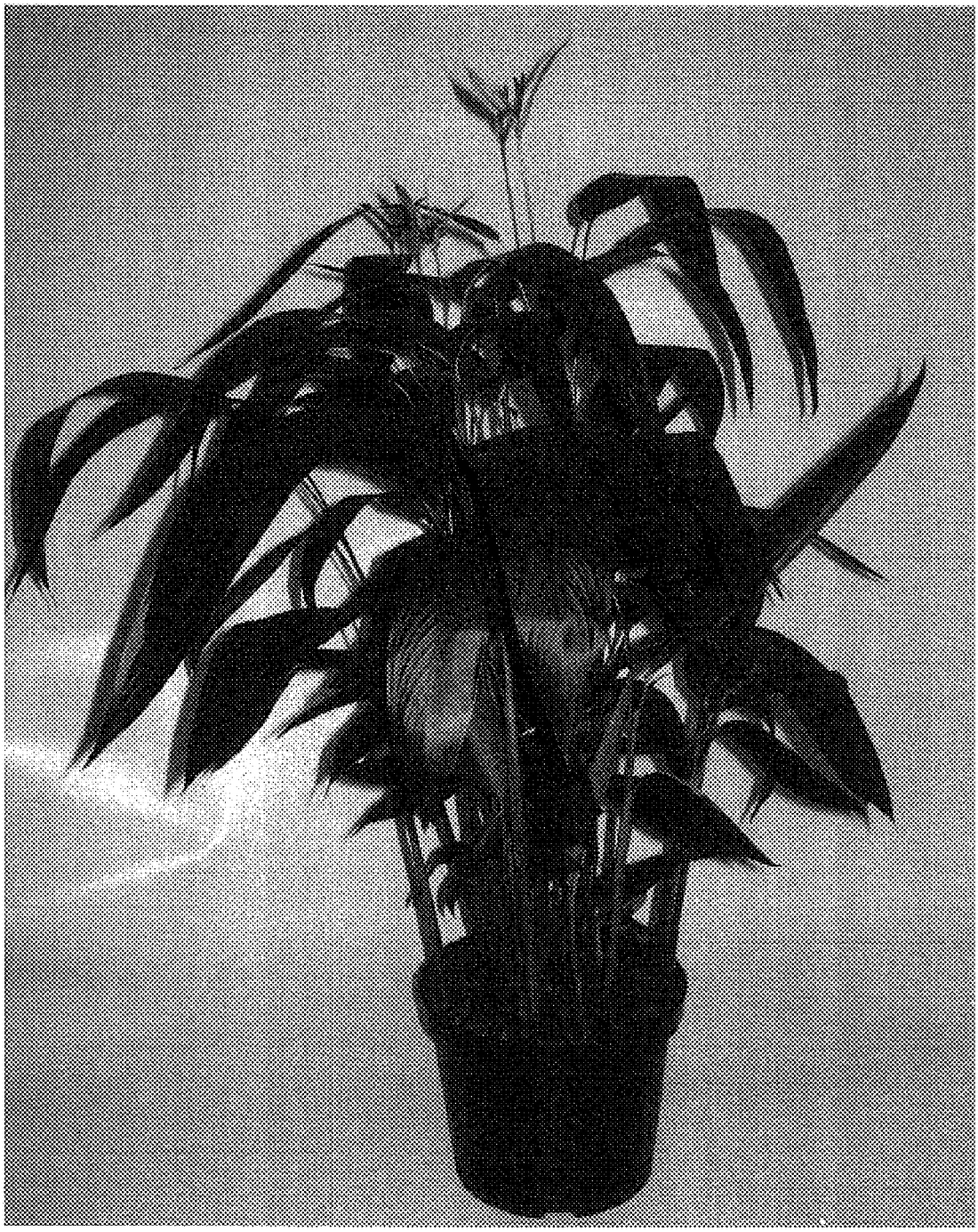

* * * * *